(12) United States Patent
Chaudhari et al.

(10) Patent No.: US 6,294,687 B1
(45) Date of Patent: Sep. 25, 2001

(54) PROCESS FOR THE PREPARATION OF SATURATED CARBOXYLIC ACIDS AND THEIR ESTERS

(75) Inventors: Raghunath Vitthal Chaudhari; A. Seayad; Jayasree Seayad, all of Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/475,555

(22) Filed: Dec. 30, 1999

(30) Foreign Application Priority Data

Jan. 9, 1999 (IN) .................................. 54/DEL/99

(51) Int. Cl.[7] .......................... C07C 67/36; C07C 67/38; C07C 51/10; C07C 51/12; C07C 51/14

(52) U.S. Cl. ......................... 560/114; 560/233; 562/406

(58) Field of Search ..................... 560/233, 114; 562/406, 233

(56) References Cited

U.S. PATENT DOCUMENTS 3,287,455 * 11/1966 Malkin et al. .
4,171,360 * 10/1979 Hill .
6,069,253 * 5/2000 Chaudhari et al. .

* cited by examiner

*Primary Examiner*—Sreeni Padmanabhan
*Assistant Examiner*—Sikarl A. Witherspoon
(74) *Attorney, Agent, or Firm*—Ladas & Parry

(57) ABSTRACT

The present invention discloses this invention relates to a process for the conversion of olefinically unsaturated compounds to corresponding carboxylic acids and their esters of formula III

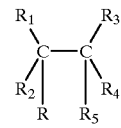

III wherein $R_1$, $R_2$, $R_3$ and R4 may independently be hydrogen, alkyl, aryl, arylalkyl, cycloaliphatic with or without substituents, R and $R_5$ may be H and COOR' or vice versa wherein R' may be H in the case of acids and may be alkyl, aryl, arylalkyl, cycloaliphatic with or without substituents, in the case of esters, wherein said conversion is carried out in the presence of a transition metal complex catalyst of the formula. a transition metal complex catalyst of the formula I

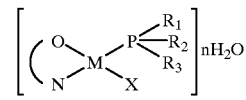

I wherein M is a group VIII metal, $R_1$, $R_2$, and $R_3$ are substituents on the phosphine ligand and are selected from hydrogen, alkyl, aryl, arylalkyl arylalkyl cycloaliphatic, X is selected from aryl or alkyl sulphonato or aryl or alkyl carbonato or formato or halides selected from $Cl^-$, $Br^-$ or $I^-$; NO is a semilabile anionic chelating ligand containing a N donor and an $O^-$ group, $1<n<10$, and a protonic acid (or hydrogen gas) and a proton source, in an organic solvent, in a carbon monoxide atmosphere in a homogeneous medium, with or without excess phosphorus ligand.

29 Claims, No Drawings

US 6,294,687 B1

PROCESS FOR THE PREPARATION OF SATURATED CARBOXYLIC ACIDS AND THEIR ESTERS

FIELD OF THE INVENTION

The present invention relates to an improved process for the preparation of saturated carboxylic acids and their esters. More particularly, this invention relates to a process for the conversion of olefinically unsaturated compounds to corresponding carboxylic acids and their esters of formula III

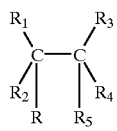

wherein $R_1$, $R_2$, $R_3$ and $R_4$ may independently be hydrogen, alkyl, aryl, arylalkyl, cycloaliphatic with or without substituents, R and $R_5$ may be H and COOR' or vice versa wherein R' may be H in the case of acids and may be alkyl, aryl, arylalkyl, cycloaliphatic with or without substituents, in the case of esters. More particularly, the present invention relates to a process for the preparation of saturated carboxylic acids and their esters using an efficient catalyst.

BACKGROUND OF THE INVENTION

The aryl and aliphatic carboxylic acids and esters have a variety of applications in industries as anti-inflammatory drugs, fine chemicals etc. The prior art describes catalyst systems for employment in processes for the preparation of esters of carboxylic acids. So far, the most preferred catalyst system has been homogeneous palladium catalysts. Generally, the various catalyst systems used for the hydrocarbonylation of olefins contains a palladium source, a phosphine ligand and a hydrogen halide promoter. Hydrocarbonylation of olefins using a catalyst system comprising $PdCl_2$ or $PdCl_2(PPh_3)_2$, excess triphenyl phosphine and HCl has been found to occur only at drastic conditions such as 300–700 atm of CO pressure.

(Bittler et al., Agnew. Chem. Internat. Edit. 7, 1968, 329). Oi et al. (J. Mot. Cat. A. Chem., 115, 1997, 289) have reported hydroesterification of styrene using cationic palladium complexes which proceeds under mild conditions (20 atm, 80° C.) to give 91 to 94% product yield in four hours (TOF=11 h$^{-1}$) with n: iso ratio of 60:40. Recently, Seayed et al (Ind. Eng. Chem. Res., 37, 1998, 2180) have shown enhanced reaction rates in the hydroesterification of styrene (TOF=41 1 h$^{-1}$) using a catalyst system comprising of $Pd(OAc)_2$, $PPh_3$ and p-toluene sulphonic acid with an n: iso ratio of 35:64. Even though, a variety of palladium phosphine complexes have been used for olefin hydroesterification, metal complexes which contain N- containing ligands have never been attempted.

Most of these catalyst systems cause disadvantages during the course of their employment for the preparation of carboxylic acids and esters. These include the requirement of severe conditions, use of excess ligands and promoters. Also, most of the conventional catalyst systems lose their efficacy on recycling.

Thus, there is a need for an improved process for the manufacture of carboxylic acids and esters wherein the yield and selectivity are good and the catalyst system is stable even in the absence of excess ligands.

The applicants have observed that the new transition metal complex containing a semilabile anionic ligand, which is a chelating organic compound containing a N-donor and an O$^-$ group, described in their co-pending U.S. patent application Ser. No. 09/281, 929 now U.S. Pat. No. 6,069, 253 is particularly suited for use as a catalyst for the preparation of saturated carboxylic acids and esters by the hydrocarbonylation of olefinically unsaturated compounds. This transition metal complex is prepared according to the process described in said co-pending application Ser. No. 09/281,929 now U.S. Pat. No. 6,069,253. The catalyst gives good yield and selectivity and the catalyst is stable even in the absence of excess ligands and can also be recycled efficiently.

OBJECTS OF THE INVENTION

It is an object of the present invention to provide an improved process for the preparation of saturated carboxylic acids and their esters by the hydrocarbonylation of olefins.

It is another object of the invention to provide a process for the preparation of saturated carboxylic acids and esters using a novel catalyst system.

It is another object of the invention to provide a process for the preparation of saturated carboxylic acids and esters thereof with an improved yield and selectivity even in the absence of excess ligands in the catalyst.

It is yet another object of the present invention to provide a process for the preparation of saturated carboxylic acids and esters thereof with an improved yield and selectivity using a catalyst which contains a N donor and an O$^-$ group for the hydrocarbonylation of olefins.

It is a further object of the invention to provide a process for the preparation of saturated carboxylic acids and their esters wherein the catalyst system substantially retains its efficiency even on recycling.

SUMMARY OF THE INVENTION

The present invention relates to an improved process for the preparation of saturated carboxylic acids and esters thereof of the formula III

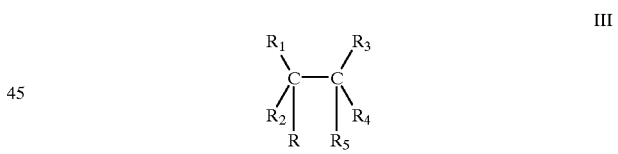

wherein $R_1$, $R_2$, $R_3$ and $R_4$ may independently be hydrogen, alkyl, aryl, arylalkyl, or cycloaliphatic group with or without substituents and R and $R_5$ may be H and COOR' or vice versa wherein R' may be H in the case of acids and may be alkyl, aryl, arylalkyl, or cycloaliphatic group with or without substituents in the case of esters, which comprises reacting an olefin of general formula II

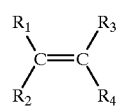

wherein $R_1$, $R_2$, $R_3$ and $R_4$ may independently be hydrogen, alkyl, aryl, arylalkyl, or cycloaliphatic group with or without substituents, with a transition metal complex catalyst of formula I

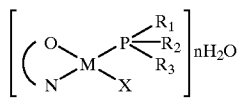

wherein M is a group VIII metal; $R_1$, $R_2$, and $R_3$ are substituents on the phosphine ligand and are selected from hydrogen, alkyl, aryl, arylalkyl, or arylalkyl cycloaliphatic group; X is selected from aryl or alkyl sulphonato or aryl or alkyl carbonate or formato or halides such as $Cl^-$, $Br^-$ or $I^-$; NO is a semilabile anionic chelating ligand containing a N donor and an $O^-$ group, $1<n<10$, and a protonic acid (or hydrogen gas) and a proton source, in an organic solvent, in a carbon monoxide atmosphere in a homogeneous medium, with or without excess phosphorus ligand, heating the mixture to a temperature between 30° C. to 120° C., for a period ranging between 30 to 180 minutes, at a pressure ranging between 1 to 40 atm, cooling the reaction mixture to ambient temperature, flushing the reaction vessel with inert gas, removing the solvent by conventional methods, separating the catalyst and isolating said compound of general formula III.

In one embodiment of the present invention, the catalyst of the formula I is prepared as described in allowed U.S. patent application Ser. No. 09/281,929 now U.S. Pat. No. 6,069,253.

In a further embodiment of the invention, the catalyst is of the general formula I

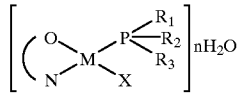

wherein M is a group VIII metal selected from palladium or platinum; $R_1$, $R_2$, and $R_3$ are substituents on the phosphine ligand and are selected from hydrogen, alkyl, aryl, arylalkyl, or arylalkyl cycloaliphatic; X is selected from aryl or alkyl sulphonato or aryl or alkyl carbonato or formato or halides such as $Cl^-$, $Br^-$ or $I^-$; NO is a semilabile anionic chelating ligand containing a N donor and an $O^-$ group such as 8-hydroxy quinoline, 2-hydroxy pyridine, 2-(2-hydroxyethyl) pyridine, pyridyl-2-, piperidyl-2-, quinolyl-2-, isoquinolyl-1- and isoquinolyl-3- carboxylates, particularly pyridyl-2- carboxylate, piperidyl-2-carboxylate, and 8-hydroxyquinoline; and $1<n<10$.

In a preferred embodiment of the invention, in the above formula I, M is $Pd^-$, $R_1$, $R_2$, and $R_3$ are phenyl; X is p-toluenesulphonato (OT's); NO is pyridyl-2-carboxylate and n is 3. The catalyst of this embodiment is referred to by the general formula Ia.

In another embodiment of the invention, the proton source used is selected from water, formic acid, acetic acid and propionic acid for the preparation of the saturated acids and any alcohol such as methanol, ethanol, and butanol and phenols are used for the preparation of the saturated esters. and any alcohol such as methanol, ethanol, butanol and phenols are used for the preparation of the saturated esters.

In yet another embodiment of the invention, the solvent used is any aprotic solvent such as aromatic hydrocarbons like benzene, toluene, or xylene; ketones like methyl ethyl ketone, or acetone; amides like N-methyl pyrrolidine; cyclic ethers such as tetrahydrofuran, or dioxan; nitriles such as acetonitrile or carboxylic acids such as formic acid, acetic acid, or propionic acid for the preparation of the saturated acids.

In a further embodiment of the invention, the alcohol itself is used as the proton source.

In another embodiment of the invention, the solvent for the preparation of the saturated esters is selected from aromatic hydrocarbons like benzene, toluene, or xylene; ketones like methyl ethyl ketone, or acetone; amides like N-methyl pyrrolidone or cyclic ethers such as tetrahydrofuran or dioxan.

In another embodiment of the invention the protonic acid used may be any of the hydrohalic acids such as hydrochloric acid, hydrobromic acid, or hydroiodic acid or other protonic acids such as para toluene sulphonic acid, methane sulphonic acid, trifluoromethane sulphonic acid, formic acid, oxalic acid, acetic acid or trifluoroacetic acid.

In yet another embodiment of the invention, the phosphorus ligand, when used, is preferably a mono phosphine, preferable selected from triphenyl phosphine, tris paratolyl phosphine, tris parachlorophenyl phosphine, tris paramethoxyphenyl phosphine, tricyclohexyl phosphine, tributyl phosphine and methyl diphenyl phosphine.

In another embodiment of the invention, the concentration of the catalyst is between 1 mole of catalyst for every 100 to 1000 moles of olefin, preferably 1 mole of catalyst for every 200 to 600 moles of olefin.

In another embodiment of the invention, the number of moles of acid promoter per gram atom of palladium in the catalyst system is in the range of 1 to 100 moles, preferably 2 to 10 in the case of preparation of saturated esters and preferably 30 to 50 in the case of preparation of saturated acids.

In yet another embodiment of the invention, the ratio of the number of moles of the mono phosphorous ligand per gram of the catalyst is in the range of 1 to 100, preferably 2 to 10.

In a further embodiment of the invention, the reaction is carried out in a stirred reactor with the catalyst being employed in a homogenous phase with a suitable solvent in the presence of carbon monoxide.

The process of the present invention uses an improved catalyst that can be recycled efficiently, does not require severe reaction parameters, and gives good yield and selectivity.

The catalyst used is a transition metal complex containing a semilabile anionic ligand that functions as a chelating organic compound. The ligand contains a N donor and an $O^-$ group. The catalyst is prepared by the process covered by our allowed U.S. patent application Ser. No. 09/281,929, now U.S. Pat. No. 6,069,253 the contents of which are specifically incorporated herein by reference. The catalyst is preferably prepared by reacting a Group VIII metal source with a semilabile anionic chelating ligand containing a N donor and an $O^-$ group, a monodentate phosphorous ligand and the corresponding protonic acid in an organic solvent by constant stirring at ambient temperature for a period ranging between 1 to 15 minutes, precipitating the product using a suitable organic solvent, washing and drying the precipitate to obtain the catalyst complex.

The catalyst may also be prepared by mixing the corresponding halide salts in a solution of the compound of Formula I where X is aryl or alkyl sulphonato or aryl or alkyl carboxylato or formato group in an organic solvent, by constant stirring at ambient temperature for 1 to 15 minutes and then subsequently filtering, drying and washing the product to obtain the catalyst complex.

The process of the invention will now be described with reference to the following examples. However, it should be noted that the following examples are purely illustrative and should not be construed to limit the scope of the present invention in any manner.

EXAMPLE 1

A 50 ml stirred autoclave was charged with the following reactants:
Styrene: 0.0144 mol
Catalyst of the formula Ia: $6.0383 \times 10^{-5}$ mol
p-toluene sulphonic acid: $3 \times 10^{-4}$ mol
Methanol: 23.5 ml The contents of the autoclave were flushed with nitrogen and then many times with carbon monoxide. Thereafter, the contents were heated to 75° C. After the temperature is attained, the autoclave was pressurized to 500 psig with carbon monoxide, stirring was started and it was observed that carbon monoxide absorption commenced immediately. For preparation of final methyl phenyl propionate product, the pressure in the autoclave was maintained constant and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 115 $h^{-1}$ and 90% conversion of styrene with a n/iso ratio of 1.24. The product was then isolated by removing the solvents and the remaining styrene by distillation and passing a solution of the resulting mixture of products and catalyst through a glass column filled with activated alumina thereby removing the catalyst and any of the other ingredients in the mixture followed by column chromatography.

EXAMPLE 2

A 50 ml stirred autoclave was charged with the following reactants:
Styrene: 0.0144 mol
Catalyst of the formula Ia: $6.0383 \times 10^{-5}$ mol
Methanol: 23.5 ml The contents of the autoclave were flushed with nitrogen and then many times with carbon monoxide. Thereafter, the contents were heated to 75° C. After the temperature is attained, the autoclave was pressurized with 50 psig hydrogen and then to 550 psig with carbon monoxide, stirring was started, and it was observed that gas absorption commenced immediately. For preparation of final methyl phenyl propionate product, the pressure in the autoclave was maintained constant using carbon monoxide and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 40 $h^{-1}$ and 95% conversion of styrene with a n/iso ratio of 1.27. The product was then isolated by removing the solvents and the remaining styrene by distillation and passing a solution of the resulting mixture of products and catalyst through a glass column filled with activated alumina thereby removing the catalyst and any of the other ingredients in the mixture followed by column chromatography.

EXAMPLE 3

A 50 ml stirred autoclave was charged with the following reactants:
Styrene: 0.0144 mol
Catalyst of the formula Ia: $6.0383 \times 10^{-5}$ mol
p-toluene sulphonic acid: $3 \times 10^{-4}$ mol
Methanol: 23.5 ml The contents of the autoclave were flushed with nitrogen and then many times with carbon monoxide. Then the autoclave was pressurized to 300 psig using ethylene and stirred well in order to saturate the solvent with ethylene gas and after saturation the pressure was kept at 250 psig. Thereafter, the contents were heated to 75° C. After the temperature is attained, the autoclave was pressurized with 500 psig of carbon monoxide, stirring was started, and it was observed that gas absorption commenced immediately. For preparation of final methyl phenyl propionate product, the pressure in the autoclave was maintained constant using carbon monoxide and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 40 $h^{-1}$ and methyipropionate selectivity of 90%. The product was then isolated by removing the solvents and the remaining styrene by distillation and passing a solution of the resulting mixture of products and catalyst through a glass column filled with activated alumina thereby removing the catalyst and any of the other ingredients in the mixture followed by column chromatography.

EXAMPLE 4

A 50 ml stirred autoclave was charged with the following reactants:
4-methylstyrene: 0.0146 mol
Catalyst of the formula Ia: $6.0383 \times 10^{-5}$ mol
p-toluene sulphonic acid: $3 \times 10^{-4}$ mol
Methanol: 23.5 ml The contents of the autoclave were flushed with nitrogen and then many times with carbon monoxide. Thereafter, the contents were heated to 75° C. After the temperature is attained, the autoclave was pressurized to 500 psig with carbon monoxide, stirring was started and it was observed that carbon monoxide absorption commenced immediately. For preparation of final product, the pressure in the autoclave was maintained constant and the progress of the reaction monitored by observing the pressure drop, and by liquid sampling. The reaction was continued until the pressure drop was too low. The reactor was then cooled and the liquid phase analyzed by gas chromatography.

The GC analysis showed TOF of 60.3 $h^{-1}$ and 85% conversion of 4-methylstyrene with a n/iso ratio of 1.16. The product was then isolated by removing the solvents and the remaining styrene by distillation and passing a solution of the resulting mixture of products and catalyst through a glass column filled with activated alumina thereby removing the catalyst and any of the other ingredients in the mixture followed by column chromatography.

EXAMPLE 5

A 50 ml stirred autoclave was charged with the following reactants:
4- isobutylstyrene: 0.0146 mot
Catalyst of the formula Ia: $6.0383 \times 10^{-5}$ mol
p-toluene sulphonic acid: $3 \times 10^{-4}$ mol
Methanol: 23.5 ml The contents of the autoclave were flushed with nitrogen and then many times with carbon monoxide. Thereafter, the contents were heated to 75° C. After the temperature is attained, the autoclave was pressurized to 500 psig with carbon monoxide, stirring was started and it was observed that carbon monoxide absorption commenced immediately. For preparation of final product, the pressure in the autoclave was maintained constant and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 55.8 $h^{-1}$ and 88% conversion of 4-isobutylstyrene with a n/iso ratio of 1.08. The product was then isolated by removing the solvents and the remaining styrene by distillation and passing a solution of the resulting mixture of products and catalyst through a glass column filled with activated alumina thereby removing the catalyst and any of the other ingredients in the mixture followed by column chromatography.

EXAMPLE 6

A 50 ml stirred autoclave was charged with the following reactants:
Styrene: 0.0146 mol
Catalyst of the formula Ia: 6.0383×10$^{-5}$ mol
p-toluene sulphonic acid: 3×10$^{-4}$ mol
Methanol: 23.5 ml The contents of the autoclave were flushed with nitrogen and then many times with carbon monoxide. Thereafter, the contents were heated to 75° C. After the temperature is attained, the autoclave was pressurized to 1000 psig with carbon monoxide, stirring was started and it was observed that carbon monoxide absorption commenced immediately. For preparation of final product, the pressure in the autoclave was maintained constant and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 115 $h^{-1}$ and 90% conversion of styrene with a n/iso ratio of 0.88. The product was then isolated by removing the solvents and the remaining styrene by distillation and passing a solution of the resulting mixture of products and catalyst through a glass column filled with activated alumina thereby removing the catalyst and any of the other ingredients in the mixture followed by column chromatography.

EXAMPLE 7

A 50 ml stirred autoclave was charged with the following reactants: Final reaction mixture of Example 1 and Styrene: 0.0146 mol The contents of the autoclave were flushed with nitrogen and then many times with carbon monoxide. Thereafter, the contents were heated to 75° C. After the temperature is attained, the autoclave was pressurized to 500 psig with carbon monoxide, stirring was started and it was observed that carbon monoxide absorption commenced immediately. For preparation of final product, the pressure in the autoclave was maintained constant and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 112 $h^{-1}$ and 91% conversion of styrene with a n/iso ratio of 1.25. The product was then isolated by removing the solvents and the remaining styrene by distillation and passing a solution of the resulting mixture of products and catalyst through a glass column filled with activated alumina thereby removing the catalyst and any of the other ingredients in the mixture followed by column chromatography.

EXAMPLE 8

A 50 ml stirred autoclave was charged with the following reactants: Final reaction mixture of Example 7 and Styrene: 0.0146 mol The contents of the autoclave were flushed with nitrogen and then many times with carbon monoxide. Thereafter, the contents were heated to 75° C. After the temperature is attained, the autoclave was pressurized to 500 psig with carbon monoxide, stirring was started and it was observed that carbon monoxide absorption commenced immediately. For preparation of final product, the pressure in the autoclave was maintained constant and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 115 $h^{-1}$ and 92% conversion of styrene with a n/iso ratio of 1.27. The product was then isolated by removing the solvents and the remaining styrene by distillation and passing a solution of the resulting mixture of products and catalyst through a glass column filled with activated alumina thereby removing the catalyst and any of the other ingredients in the mixture followed by column chromatography.

EXAMPLE 9

A 50 ml stirred autoclave was charged with the following reactants:
Styrene: 0.0146 mol
Catalyst of the formula Ia: 6.0383×10$^{-5}$ mol
Triphenyl phosphine: 6.0383×10$^{-5}$ mol
p-toluene sulphonic acid: 3×10$^{-4}$ mol
Methanol: 23.5 ml The contents of the autoclave were flushed with nitrogen and then many times with carbon monoxide. Thereafter, the contents were heated to 75° C. After the temperature is attained, the autoclave was pressurized to 5000 psig with carbon monoxide, stirring was started and it was observed that carbon monoxide absorption commenced immediately. For preparation of final product, the pressure in the autoclave was maintained constant and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 125 $h^{-1}$ and 87% conversion of styrene with a n/iso ratio of 1.3. The product was then isolated by removing the solvents and the remaining styrene by distillation and passing a solution of the resulting mixture of products and catalyst through a glass column filled with activated alumina thereby removing the catalyst and any of the other ingredients in the mixture followed by column chromatography.

EXAMPLE 10

A 50 ml stirred autoclave was charged with the following reactants: Final reaction mixture of Example 9 and Styrene: 0.0146 mol The contents of the autoclave were flushed with nitrogen and then many times with carbon monoxide. Thereafter, the contents were heated to 75° C. After the temperature is attained, the autoclave was pressurized to 500 psig with carbon monoxide, stirring was started and it was observed that carbon monoxide absorption commenced immediately. For preparation of final product, the pressure in the autoclave was maintained constant and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 123 $h^{-1}$ and 87.4% conversion of styrene with a n/iso ratio of 1.27.

EXAMPLE 11

A 50 ml stirred autoclave was charged with the following reactants: Final reaction mixture of Example 10 and Styrene: 0.0146 mol The contents of the autoclave were flushed with nitrogen and then many times with carbon monoxide. Thereafter, the contents were heated to 75° C. After the temperature is attained, the autoclave was pressurized to 500 psig with carbon monoxide, stirring was started and it was observed that carbon monoxide absorption commenced immediately. For preparation of final product, the pressure in the autoclave was maintained constant and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 130 $h^{-1}$ and 90% conversion of styrene with a n/iso ratio of 1.5.

EXAMPLE 12

A 50 ml stirred autoclave was charged with the following reactants:
Styrene: 0.0146 mol
Catalyst of the formula Ia: $6.0383 \times 10^{-5}$ mol
Triphenyl phosphine: $6.0383 \times 10^{-5}$ mol
Formic acid: 0.022 mols
Toluene (solvent): 0.0239 mols The contents of the autoclave were flushed with nitrogen and then many times with carbon monoxide. Thereafter, the contents were heated to 75° C. After the temperature is attained, the autoclave was pressurized to 500 psig with carbon monoxide, stirring was started and it was observed that carbon monoxide absorption commenced immediately. For preparation of the final product, the pressure in the autoclave was maintained constant and the progress of the reaction monitored by observing the pressure drop and by liquid sampling. The reaction was continued until the pressure drop was too low. The reactor was then cooled and the liquid phase analyzed by gas chromatography.

The GC analysis showed TOF of 180 $h^{-1}$ and 95% conversion of styrene with a n/iso ratio of 0.85.

The final reaction mixture was washed with water many times to remove formic acid and then extracted with 10% NaOH solution to get the sodium salt of 2-phenylpropionic acid in the NaOH layer. The NaOH layer was separated and acidified with 10% HCl and extracted by diethyl ether which on subsequent evaporation and column chromatography gave the product.

Advantages of the invention:
1. The invention provides an improved process for the preparation of saturated carboxylic acids and their esters using a novel catalyst.
2. The invention provides a simple and efficient catalyst recycling.
3. The invention avoids the use of excessive ligands.

What is claimed is:
1. A process for the preparation of saturated carboxylic acids and esters of formula III

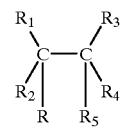

wherein $R_1$, $R_2$, $R_3$ and $R_4$ are independently hydrogen, or substituted or unsubstituted alkyl, aryl, arylalkyl, or cycloaliphatic group; when R is hydrogen, $R_5$ is COOR' and when R is COOR', R is hydrogen, R' is hydrogen or substituted or unsubstituted alkyl, aryl, arylalkyl, or cycloaliphatic group which comprises the steps of
a) reacting an olefin of formula II

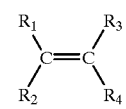

wherein $R_1$, $R_2$, $R_3$ and $R_4$ are as defined above, with a transition metal complex of the formula I

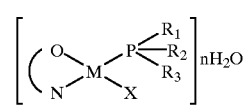

wherein M is a group VIII metal; $R_1$, $R_2$ and $R_3$ are substitutents on the phosphine ligand and are selected from hydrogen, alkyl, aryl, arylalkyl, or arylalkyl cycloaliphatic group; X is selected from aryl sulphonato, alkyl sulphonato, aryl carbonate, alkyl carbonate, formato or halides selected from Cl$^-$, Br$^-$ or I$^-$; NO is a semilabile anionic chelating ligand containing a N donor and an O$^-$ group, wherein 1<n<10, with a protonic acid or hydrogen gas and a proton source, in an organic solvent, in a carbon monoxide atmosphere in a homogeneous medium, with or without excess phosphorus ligand,
b) heating the mixture to a temperature between 30° C. to 120° C., for a period ranging between 30 to 180 minutes, at a pressure ranging between 1 to 40 atm,
c) cooling the reaction mixture to ambient temperature,
d) flushing with inert gas,
e) removing the solvent,
f) separating the catalyst; and
g) isolating the compound of formula III.
2. The process as claimed in claim 1 wherein in the catalyst of formula I, M is selected from palladium or platinum, $R_1$, $R_2$ and $R_3$ are selected from hydrogen, alkyl, aryl, arylalkyl or arylalkyl cycloaliphatic, X is selected from aryl sulphonato, alkyl sulphonato, aryl carbonate, or alkyl carbonate, or formato group or halides selected from Cl$^-$, Br$^-$ or I$^-$, and NO the semilabile anionic chelating ligand is selected from the group consisting of 8-hydroxy quinoline, 2-hydroxy pyridine, 2-(2-hydroxyethyl)pyridine; and pyridyl-2-, piperidyl-2-quinolyl-2-, isoquinolyl-1- and isoquinolyl-3-carboxylates, and 1<n<10.

3. The process as claimed in claim 2 wherein M is palladium; $R_1$, $R_2$, and $R_3$ are phenyl; X is p-toluenesulphonato; NO is pyridyl-2-carboxylate and n is 3.

4. The process as claimed in claim 1 for the preparation of a saturated carboxylic acid wherein the proton source is selected from the group consisting of water, formic acid, acetic acid and propionic acid.

5. The process as claimed in claim 1 for the preparation of a saturated ester wherein the proton source is an alcohol selected from the group consisting of methanol, ethanol, butanol and phenol.

6. The process as claimed in claim 1, for the preparation of a saturated carboxylic acid wherein the solvent is an aprotic solvent selected from an aromatic hydrocarbon, a ketone, an amide, a cyclic ether, a nitrile, or a carboxylic acid.

7. The process as claimed in claim 1, wherein the solvent for the preparation of the saturated ester is selected from an aromatic hydrocarbon, a ketone, an amide or a cyclic ether.

8. The process as claimed in claim 1, wherein the protonic acid is a hydrohalic acid.

9. The process as claimed in claim 1, wherein the phosphorous ligand is a monophosphine.

10. The process as claimed in claim 1, wherein the phosphorous ligand is selected from the group consisting of triphenyl phosphine, tris paratolyl phosphine, tris parachlorophenyl phosphine, tris paramethoxyphenyl phosphine, tricyclohexyl phosphine, tributyl phosphine and methyl diphenyl phosphine.

11. The process as claimed in claim 1, wherein the molar ratio of catalyst to olefin is 1:100–1000.

12. The process as claimed in claim 2, wherein the number of moles of acid promoter per gram atom of palladium in the catalyst system is in the range of 1 to 100 moles.

13. The process as claimed in claim 12, for the preparation of a saturated acid wherein the number of moles of acid promoter per gram of palladium in the catalyst system is 2 to 10.

14. The process as claimed in claim 12, for the preparation of a saturated acid wherein the number of moles of acid promoter per gram of palladium in the catalyst system is 30 to 50.

15. The process as claimed in claim 1, wherein the number of moles of the mono phosphorous ligand per gram of the catalyst is in the range of 1 to 100.

16. The process according to claim 6, wherein the aromatic hydrocarbon is selected from benzene, toluene or xylene.

17. The process according to claim 6, wherein the ketone is selected from methylethylketone or acetone.

18. The process according to claim 6, wherein the amide is N-methyl pyrrolidine.

19. The process according to claim 6, wherein the cyclic ether is selected from tetrahydrofuran or dioxan.

20. The process according to claim 6, wherein the nitrile is acetonitrile.

21. The process according to claim 6, wherein the carboxylic acid is formic acid, acetic acid or propionic acid.

22. The process according to claim wherein the aromatic hydrocarbon is selected from benzene, toluene or xylene.

23. The process according to claim 7, wherein the ketone is selected from methylethylketone or acetone.

24. The process according to claim 7, wherein the amide is N-methyl pyrrolidine.

25. The process according to claim 7, wherein the cyclic ether is selected from tetrahydrofuran or dioxan.

26. The process according to claim 8, wherein the hydrohalic acid is hydrochloric acid, hydrobromic acid or hydroiodic acid.

27. The process as claimed in claim 1, wherein the protonic acid is selected from the group consisting of paratoluene sulphonic acid, methane sulphonic acid, trifluoromethane sulphonic acid, formic acid, oxalic acid, acetic acid and trifluoroacetic acid.

28. The process according to claim 11, wherein the molar ratio of catalyst to olefin is 1:200–600.

29. The process according to claim 15, wherein the number of moles of the monophorous ligand per gram of catalyst is 2 to 10.

* * * * *